United States Patent

Schneider et al.

[11] Patent Number: 5,902,470
[45] Date of Patent: May 11, 1999

[54] SENSOR ELEMENT

[75] Inventors: Gerhard Schneider, Vaihingen; Hans-Joerg Renz, Leinfelden-Echterdingen; Harald Neumann, Vaihingen, all of Germany

[73] Assignee: Robert Bosch GmbH, Stuttgart, Germany

[21] Appl. No.: 08/952,204

[22] PCT Filed: Oct. 23, 1996

[86] PCT No.: PCT/DE96/02031

§ 371 Date: Nov. 7, 1997

§ 102(e) Date: Nov. 7, 1997

[87] PCT Pub. No.: WO97/33163

PCT Pub. Date: Sep. 12, 1997

[30] Foreign Application Priority Data

Mar. 9, 1996 [DE] Germany ............... 196 09 323

[51] Int. Cl.⁶ ............................................. G01N 27/407
[52] U.S. Cl. ................................... 204/427; 204/426
[58] Field of Search ................................ 204/421–429; 205/783.5, 784

[56] References Cited

U.S. PATENT DOCUMENTS

| | | | |
|---|---|---|---|
| 4,541,900 | 9/1985 | Mase et al. | 204/1 T |
| 4,900,412 | 2/1990 | Ker et al. | 204/427 |
| 5,296,112 | 3/1994 | Seger et al. | 204/153.18 |
| 5,395,506 | 3/1995 | Duce et al. | 204/426 |

FOREIGN PATENT DOCUMENTS

| | | |
|---|---|---|
| 0134709 | 3/1985 | European Pat. Off. . |
| 0390337 | 10/1990 | European Pat. Off. . |
| 3729164 | 4/1988 | Germany . |
| 2054868 | 2/1981 | United Kingdom . |

Primary Examiner—T. Tung
Assistant Examiner—Jennifer McNeil
Attorney, Agent, or Firm—Venable; George H. Spencer; Ashley J. Wells

[57] ABSTRACT

The invention relates to a sensor element, particularly for an electrochemical measuring sensor, for determining the oxygen content of gases, having a first electrode, which is exposed to a gas to be measured, a second electrode, which is exposed to a reference gas, a heating device for the sensor element and a reference gas conduit extending between the heating device and the second electrode.

It is provided that the reference gas conduit (20) is configured so as to be branched at least in the region of the heating device (30).

6 Claims, 1 Drawing Sheet

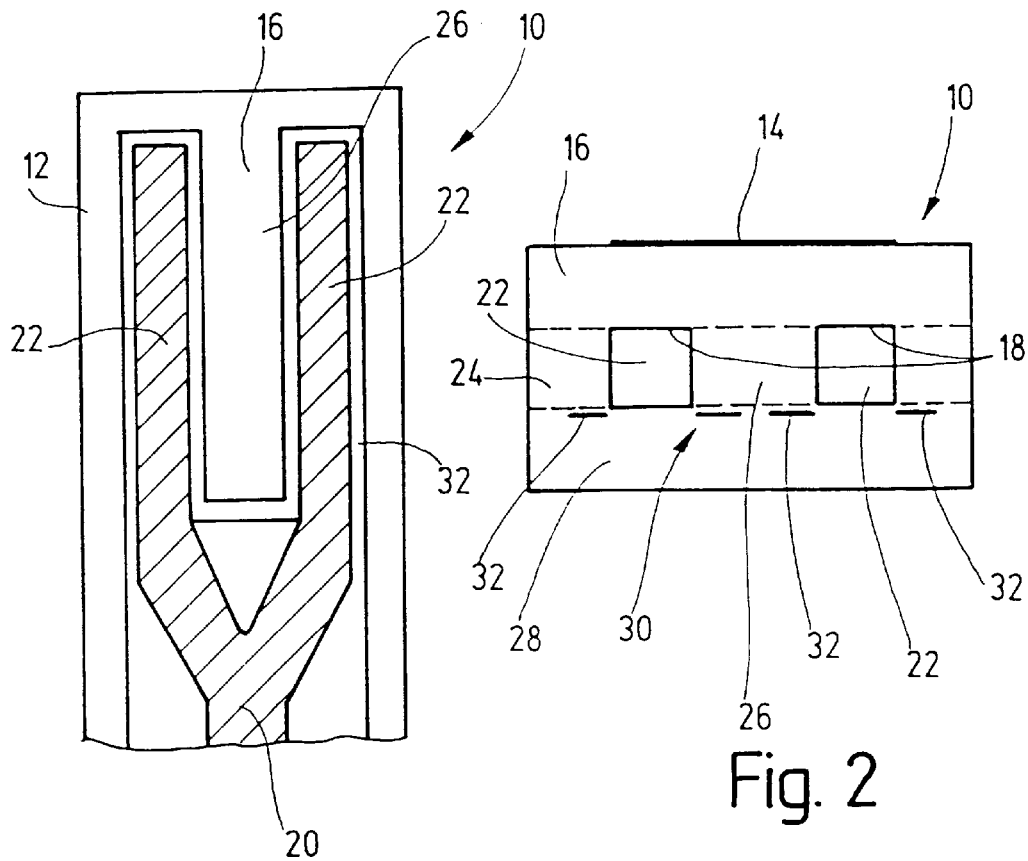
Fig. 1
Fig. 2
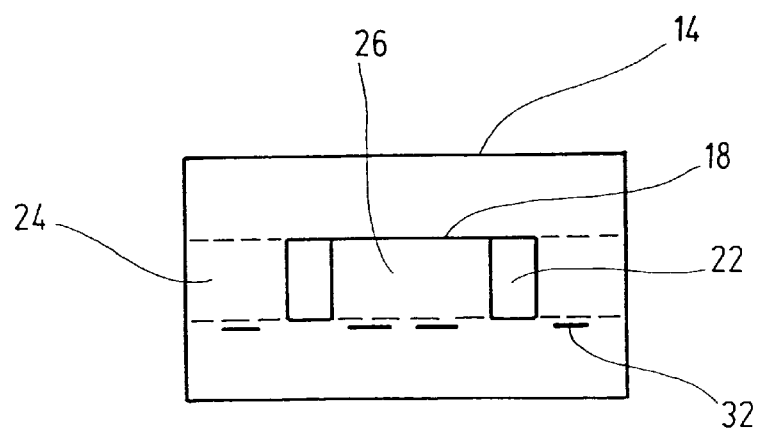
Fig. 3

SENSOR ELEMENT

The invention relates to a sensor element for an electrochemical measuring sensor for determining the oxygen content of gases, particularly for determining the oxygen content in exhaust gases of internal combustion engines, the sensor element having the features cited in the preamble of claim 1.

STATE OF THE TECHNOLOGY

Sensor elements of the generic type are known. They are designed, e.g., as so-called planar sensor elements, having a first electrode on a solid electrolyte formed as a carrier, which electrode is exposed to a gas to be measured, and a second electrode exposed to a reference gas. For various applications, the sensor element must be heated to a certain temperature. For this purpose, it is known to allocate to the sensor element a heating device which usually has heating conductors extending below the electrode that is exposed to the reference gas.

In order to supply a reference gas to the reference gas electrode, a reference gas conduit is provided within the planar sensor element which is constructed in layers, which conduit extends, for example, in the longitudinal direction of the sensor element. This reference gas conduit extends between the reference gas electrode and the heating conductors.

An electrochemical measuring sensor with a sensor element of this type is disclosed, e.g., in DE 29 28 496. It has the drawback that the reference gas conduit is a poor heat conductor for the thermal energy emitted by the heating device so that the sensor element can only be heated to its operating temperature with an increased heating energy or after a correspondingly long heating time. The heat transfer to the sensor element is poor, particularly in sensor elements in which the heating conductors are in direct connection with the reference gas conduit.

ADVANTAGES OF THE INVENTION

In contrast, the sensor element according to the invention having the features stated in claim 1 offers the advantage that a heat transfer from the heating device to the sensor element is considerably improved. Since the reference gas conduit is designed so as to be divided, at least in the region of the heating device, there is the possibility of matching the layout of the reference gas conduit and/or of the heating device in such a manner that a heat conduction between the heating device and the sensor element can be assumed by the substrate disposed between the divided (branched) reference gas conduits. This substrate has a much better thermal conductivity than the reference gas in the reference gas conduits so that heat can be transferred more quickly and more effectively. Thus it is possible, in particular, to accomplish a shorter heating-up period for the sensor element or a higher sensor element temperature with a predetermined heating power of the heating device. On the other hand, it is possible to reduce the heating power of the heating device while maintaining the heating-up time and the same sensor element temperature so that an improved long-term stability of the heating device and an improved thermal shock behavior of the sensor element can be accomplished. In addition, the branching of the reference gas conduit in the region of the heating device increases the mechanical stability of the entire planar sensor element because ribs remaining between the individual branches of the reference gas conduit provide for a smaller unsupported width of the reference gas conduit.

A further advantage of the sensor element according to the invention results from the fact that there is no longer any overlap between the width of the reference gas conduit and an insulating system for the heating conductors. This prevents damage to the insulating system in the region of the heating conductors during the production of the sensor elements, particularly during the lamination of the individual layers of the sensor elements. Minimizing or excluding any damage of the insulating system results in an improved leakage current behavior of the heating conductors.

Advantageous embodiments of the invention ensue from the remaining features that are cited in the dependent claims.

DRAWINGS

The invention is explained below in detail by way of embodiments with reference to the associated drawings. These show:

FIG. 1 a longitudinal section through a sensor element according to the invention;

FIG. 2 a cross section through the sensor element according to FIG. 1, and

FIG. 3 a cross section through a sensor element of the invention according to a further embodiment.

DESCRIPTION OF THE EMBODIMENTS

FIG. 1 shows a cut-open longitudinal view of a portion of a sensor element 10. The sensor element 10 is a component of an electrochemical measuring sensor, not shown, and is fixed tightly in a housing of the measuring sensor. The sensor element 10 has a planar layered design which is explained in greater detail by way of FIG. 2. FIG. 1 shows a section 12 of the sensor element 10 on the side of the gas to be measured. The sensor element 10 also has a section on the side of the reference gas, not shown. The sensor element 10 has a first electrode 14 which can be exposed to a gas to be measured, e.g., the exhaust gas of a motor vehicle. Here, the electrode 14 is applied on a solid electrolyte, for example, stabilized zirconium oxide, which simultaneously serves as carrier 16. On its side facing away from the electrode 14, the carrier 16 has a second electrode 18 which can be exposed to a reference gas, for example, to the atmospheric oxygen. For the feeding of the reference gas, the sensor element 10 has a reference gas conduit 20 extending in longitudinal direction. The reference gas conduit 20 branches out into two reference gas conduit arms 22 extending below the electrode 18 which also splits accordingly. The reference gas conduit 20 or the reference gas conduit arms 22 are patterned in a substrate 24. The branching of the reference gas conduit 20 produces closed regions 26 of the substrate 24 between the reference gas conduit arms 22.

The representation shown in FIGS. 1 and 2 with two reference gas conduit arms 22 is only used by way of example. This means that it is possible, of course, to divide the reference gas conduit 20 into several individual arms. In addition, transverse connections between the individual arms are possible. The decisive point is that regions 26 of the substrate 24 remain between the individual reference gas conduit arms 22.

Arranged below the substrate 24 is a further substrate layer 28 which contains a heating device 30 for the sensor element 10. The heating device 30 has heating conductors 32 which extend in a meandering manner and are arranged such that they are covered respectively by the substrate 24 or by the regions 26 of the substrate 24. Thus, the extension of the heating conductors 32 is such that there is no direct connection to the reference gas conduit arms 22.

By means of the arrangement selected in FIGS. 1 and 2 of the reference gas conduit arms 22 relative to the heating conductors 32, it is accomplished that the heating conductors 32 are surrounded on all sides by the substrate of the substrate layer 28 and the substrate 24 or the regions 26 of substrate 24. This assures a good heat conduction of the thermal energy supplied via the heating conductors 32 into the sensor element 10 to the carrier 16 provided with the electrodes 14 and 18. Thus, the reference gas conduit arms 22 exert only an extremely small insulation effect on the heat transfer.

It may be advantageous to limit the splitting of the reference gas conduit 20 into reference gas conduit arms 22 to the active effective region of the heating device 30 so that, throughout the entire sensor element, only a reference gas conduit 20 is provided which runs in the longitudinal extension. Advantageously, the electrode 18 which is exposed to the reference gas is split analogously to the reference gas conduit arms 22 so that all sides of the reference gas conduit arms 22 facing the carrier 16 are covered by a region of electrode 18.

The improved heat transfer from the heating device 30 to the actual sensing region of the sensor element 10 has the effect that a shorter heating-up time of the sensor element 10 is possible while the heating power remains the same. On the other hand, the heating power can be reduced so that the overall long-term stability of the heating device 30 or of the sensor element 10 is improved. A lower heating power simultaneously leads to an improved thermal shock behavior of the sensor element 10, i.e., if the sensor element 10 suddenly comes into contact with a cooler medium, for example, splashed water, condensation water or the like, the temperature difference at a lesser heating power is not quite so high. On the other hand, it is possible to select a higher temperature of the sensor element 10 so that a lowering of the internal resistance of the electrodes 14 and 18, and thus a reduction of their power loss and the resulting negative influence on the measurement result can be reduced. Finally, the regions 26 of the substrate 24 contribute to a higher mechanical stability of section 12 of the sensor element 10 so that, due to the splitting of the reference gas conduit 20 into individual reference gas conduit arms 22, an unsupported reference gas conduit width in the region of section 12 is reduced.

In the cross section through a sensor element 10 shown in FIG. 3, parts which are identical to those in FIGS. 1 and 2 are provided with the same reference numerals and are not explained again. In contrast to this, the electrode 18 which is exposed to the reference gas is configured without interruption so that, even between the regions 26 of the substrate 24 and the carrier 16, sections of electrode 18 remain. This affects the measuring precision of the sensor element 10.

In the embodiment shown in FIG. 3, the reference gas conduit arms 22 are furthermore made to be narrower than the distance between the heating conductors 32, so that the heating conductors extend at a greater distance from the reference gas conduit arms 22. This accomplishes that the heat conduction via the substrate 24 or the region 26 of the substrate 24 to the electrodes 18 or 14 is improved because the heat conduction via substrate 24 or region 26 is greater than a heat radiation across the reference gas conduit arms 22.

Within the framework of the present description it is not intended to explain the production steps of the sensor element 10 in greater detail because the latter can be produced by means of known process steps such as film casting, printing, stamping, milling or embossing.

We claim:

1. A sensor element, particularly for an electrochemical measuring sensor, for determining the oxygen content of gases, having at least one first electrode which is exposed to a gas to be measured, at least one second electrode exposed to a reference gas, at least one heating device for the sensor element and a reference gas conduit extending between the heating device and the second electrode, characterized in that the reference gas conduit (20) is configured to be branched at least in the region of the heating device (30).

2. A sensor element according to claim 1, characterized in that the reference gas conduit (20) splits to form reference gas conduit arms (22) which extend within a substrate (24) in such a manner that heating conductors (32) of the heating device (30) extending in a substrate layer (28) do not have a direct connection to the reference gas conduit arms (22).

3. A sensor element according to claim 1, characterized in that all sides of the reference gas conduit arms (22) facing a carrier (16) are each covered by a region of the second electrode (18).

4. A sensor element according to claim 1, characterized in that the second electrode (18) extends across regions (26) of the substrate (24) disposed the reference gas conduit arms (22).

5. A sensor element according to claim 1, characterized in that two reference gas conduit arms (22) are provided which extend within free spaces of a heating conductor (32) arranged in a meandering manner.

6. A sensor element according to claim 1 characterized in that the heating conductors (32) of the heating device (30) extend at a distance from the branched reference gas conduit arms (22).

* * * * *